US008833365B2

(12) United States Patent
Mayer et al.

(10) Patent No.: US 8,833,365 B2
(45) Date of Patent: Sep. 16, 2014

(54) DOSING DEVICE FOR GENERATING A GAS FLOW WITH A FINELY DISPERSED ACTIVE SUBSTANCE

(75) Inventors: Stefan Mayer, Freiburg Im Breisgau (DE); Yorick Kamlag, Pahl (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 209 days.

(21) Appl. No.: 13/141,324

(22) PCT Filed: Dec. 10, 2009

(86) PCT No.: PCT/EP2009/066829

§ 371 (c)(1),
(2), (4) Date: Oct. 19, 2011

(87) PCT Pub. No.: WO2010/072575

PCT Pub. Date: Jul. 1, 2010

(65) Prior Publication Data

US 2012/0111326 A1 May 10, 2012

(30) Foreign Application Priority Data

Dec. 23, 2008 (EP) .................................... 08172765

(51) Int. Cl.
*A61M 15/00* (2006.01)

(52) U.S. Cl.
CPC ..... *A61M 15/0065* (2013.01); *A61M 2202/064* (2013.01); *A61M 15/0025* (2014.02)
USPC ............ 128/203.15; 128/200.21; 128/203.23; 128/203.24

(58) Field of Classification Search
USPC ............ 128/200.14, 200.21, 203.12, 203.15, 128/203.19, 203.21, 203.24; 277/306, 399, 277/434, 436, 440
See application file for complete search history.

(56) References Cited

U.S. PATENT DOCUMENTS 3,374,308 A * 3/1968 Haas ......................... 174/138 R
5,592,975 A * 1/1997 Wissmann et al. ........... 138/112

(Continued)

FOREIGN PATENT DOCUMENTS

EP 1020233 A1 7/2000
EP 1905472 A2 4/2008

(Continued)

OTHER PUBLICATIONS

Phadke, D.S., et al, Evaluation of Particle Size Distribution and Specific Surface Area of Magnesium Stearate, 1991, Drug Development and Industrial Pharmacy, 17(6), 901-906.*

(Continued)

*Primary Examiner* — Justine Yu
*Assistant Examiner* — Timothy Stanis
(74) *Attorney, Agent, or Firm* — McDonnell Boehnen Hulbert & Berghoff LLP

(57) ABSTRACT

A dosing device generating a gas flow with an active substance finely dispersed, with a first gas flow channel and with a dosing chamber that can be fitted in the area of the first gas flow channel, and a dosing chamber release mechanism with a separating element. The first gas flow channel and/or a connection between the first gas flow channel and the dosing chamber is blocked when the separating element is in a closed position. The first gas flow channel and/or the connection between the first gas flow channel and the dosing chamber is freed when the separating element is in an open position. A slide guide element can be driven by the under-pressure applied to the mouthpiece. The separating element and/or the slide guide element is provided with a slide element that influences the sliding friction properties.

15 Claims, 7 Drawing Sheets

(56) References Cited

U.S. PATENT DOCUMENTS

| | | | |
|---|---|---|---|
| 5,617,845 A * | 4/1997 | Poss et al. | 128/203.15 |
| 6,105,968 A * | 8/2000 | Yeh et al. | 277/399 |
| 2002/0006919 A1 * | 1/2002 | Thosar et al. | 514/175 |
| 2004/0035417 A1 | 2/2004 | Ottolangui | |
| 2004/0035421 A1 * | 2/2004 | Schuckmann | 128/203.15 |
| 2006/0118106 A1 * | 6/2006 | Schuckmann | 128/200.14 |
| 2007/0289593 A1 * | 12/2007 | von Schuckmann | 128/203.15 |
| 2010/0295254 A1 * | 11/2010 | Tabata et al. | 277/550 |

FOREIGN PATENT DOCUMENTS

| | | |
|---|---|---|
| EP | 1905473 A2 | 4/2008 |
| JP | 2004510557 A | 4/2004 |
| RU | 2198740 C1 | 2/2003 |
| RU | 2221552 C2 | 1/2004 |
| WO | 2006021546 A1 | 3/2006 |
| WO | 2009065708 A2 | 5/2009 |

OTHER PUBLICATIONS

Carley, James F, Whittington's Dictionary of Plastics, 3rd Edition, CRC Press, 1993, p. 290.*

Japanese Patent Application No. 2011-542756, Notice of Reasons for Rejection dated Oct. 22, 2013.

Translation of Japanese Patent Application No. 2011-542756, Notice of Reasons for Rejection dated Oct. 22, 2013.

Carley, James F.: "Whittington's Dictionary of Plastics, 3rd Edition", CRC Press, 1993, p. 290.

Phadke, D.S. et al.: "Evaluation of Particle Size Distribution and Specific Surface Area of Magnesium Stearate", Drug Development and Industrial Pharmacy, 1991, 17(6), pp. 901-906.

* cited by examiner

DOSING DEVICE FOR GENERATING A GAS FLOW WITH A FINELY DISPERSED ACTIVE SUBSTANCE

CROSS REFERENCE TO RELATED APPLICATIONS

The present application is a 35 U.S.C. 371 National Application of PCT/EP2009/066829 filed Dec. 10, 2009 and claims priority to European Patent Application No. 08172765.3, filed Dec. 23, 2008, the entire contents of which are incorporated entirely herein by reference.

The invention applies to the area of medical engineering, but can also be used advantageously elsewhere.

The invention relates especially to a dosing device for generating a gas flow with an active substance finely dispersed in said gas flow.

These types of dosing devices are used in particular for inhaling active substances. In a particularly advantageous manner, such devices can be used to inhale pulverulent substances which are arranged in a storage chamber and, for a single inhalation, can be removed by means of a dosing device and introduced into a suction air stream. This can occur, for example, by removing a closure flap and at the same time actuating a dosing rod, which is movable into a ready-to-empty position with the removal of the closure flap.

Next, the person using the dosing device, by applying a negative pressure, i.e. by orally sucking in, can then generate the air flow in the dosing device which causes the necessary mechanisms within the dosing device in order to distribute the active substance finely in a suction air stream and conduct it away through the mouthpiece.

A dosing device of this type is already known from WO 2006/021546 A1.

It has also been proposed, in particular, to provide a piston which, by means of the initiating of the suction air stream, is moved to release the dosing chamber such that said dosing chamber, in which a dosed amount of the active substance is situated, can be combined with the suction air stream in order to distribute the active substance in the suction air stream.

Against the background of the prior art, it is the object of the present invention to develop, in an advantageous manner, a mechanism for releasing the dosing chamber and, in this way, to contribute to the dosing chamber being released in a reproducible and extremely reliable manner at the correct moment during the generation of the suction air stream.

The object is achieved in an advantageous manner with the features of claim 1.

In this case, the dosing device according to the invention has a first gas flow channel and a dosing chamber, which is situated at least sometimes in the region of the first gas flow channel, as well as a dosing chamber release mechanism which has a separating element which can be displaced between a closed position and an open position such that the first gas flow channel and/or a connection between the first gas flow channel and the dosing chamber can be selectively blocked or released, wherein the separating element is displaceable on a slide guide element between the closed position and the open position and is driveable by means of a negative pressure applied at the mouthpiece, and wherein the separating element and/or the slide guide element is provided at least in the sliding contact region with a slide element that influences the sliding friction properties.

In principle, the slide element provides defined sliding conditions between the separating element on the one hand and the slide guide element on the other. In this way, a sticking or jamming of the driveable separating element is prevented and the conditions for the acceleration of the separating element by means of the drive through the suction air stream are established in a reproducible manner, such that the moment at which the separating element releases the dosing chamber can also be kept to in a reproducible manner.

In this case, it can be provided in an advantageous manner that the separating element is tulip-shaped and that the slide element is provided in that part of the separating element that is widened in a tulip-shaped manner, in particular at the free end thereof on the edge on the peripheral side.

The slide element can be formed in an advantageous manner by enhancement of the separating element and/or of the slide guide element at least in the surface region with a friction-reducing or friction-determining substance.

In this case, the separating element and/or the slide guide element can contain said friction-reducing/friction-determining substance as an ingredient of the mixture or can be coated with said substance.

The substance can be present as a powder and for example can be metal soap, in particular in the form of magnesium stearate.

The advantage of coating with a powder of this type is that the friction-determining effect is achieved even with layer thicknesses within the u range such that the form of the friction partners is not changed substantially by the coating and no postprocessing is necessary. Such powders that have a specific surface between 2 and 20 square m/gram, in particular between 2.3 and 9.3 square m/gram, preferred between 3 and 8 square m/gram and further preferred between 3 and 5 square m/gram can be used in a particularly advantageous manner.

A further embodiment of the invention provides that the slide element is formed by a surface contour that has projections. In this case, the projections can be designed as knobs or webs which extend, in particular, in the sliding direction. The corresponding projections are advantageously rounded and can be provided on the separating element or else on the slide guide element. In an advantageous manner, 3 to 20, preferably 6 to 12 knobs can be provided distributed in a uniform manner over the periphery. They can be arranged at the free end of the widened part of the tulip-shaped separating element.

It is also conceivable to form corresponding projections and, in addition, to apply a friction-determining additive as an ingredient of the mixture or as a coating at the same time.

The invention is shown below by way of an exemplary embodiment in a drawing and is then described, in which.

The dosing device for inhaling an active substance 2 represented in the figures provides a manually operable, cylindrical, bar-shaped pocket device for a person and has a housing 3 and a protective cap 7 which has to be removed from the device at the start of use.

To this end the protective cap 7 has an internal thread which interacts with an external thread 9 of the housing 3.

When the protective cap 7 is unscrewed, ribs 10 on an outer cylinder 4 of the device additionally interact with grooves 11 on the inner surface of the protective cap 7 such that, when the protective cap 7 is twisted off, part of the dosing device is set into rotation in relation to the housing 3 and, as a result, a rotating part 28 which is connected to a rotor R, which acts as powder breaking device and is designed in an asymmetrical manner, is rotated such that at each use the active substance 2 in the storage chamber 15 is moved.

In the closed state of the dosing device, a dosing rod 33 in the form of a dosing sword with a dosing chamber 14, which is situated at its end region and is designed as a continuous, conical opening, enters the storage chamber 15 and, in the course of the unscrewing movement, is rotated inside the storage chamber. This ensures a filling of the dosing chamber 14 with the active substance.

On its end opposite the dosing chamber 14, the dosing rod 33 has a docking point 41 with a latching head 45 and an annular groove 46, which interacts in the closed position with lugs 47 of a longitudinally-slotted hollow cylinder 43 connected to the protective cap.

Thus, by means of the continuous axial lift of the protective cap 7 during the screwing movement, the dosing rod, pulled by the lugs 47 of the hollow cylinder 43, can be completely pulled out of the storage chamber 15 until the dosing chamber 14 lies in the region of the gas flow channel 60, 61, 62, 63, 68, which leads from an inlet region 60 via the interior of the dosing device as far as to the opening 48 in the mouthpiece 6.

Once the protective cap has been removed, by sucking in at the mouthpiece 6, air is sucked in through said first gas flow channel and consequently a partial gas flow is generated.

Figure 1:
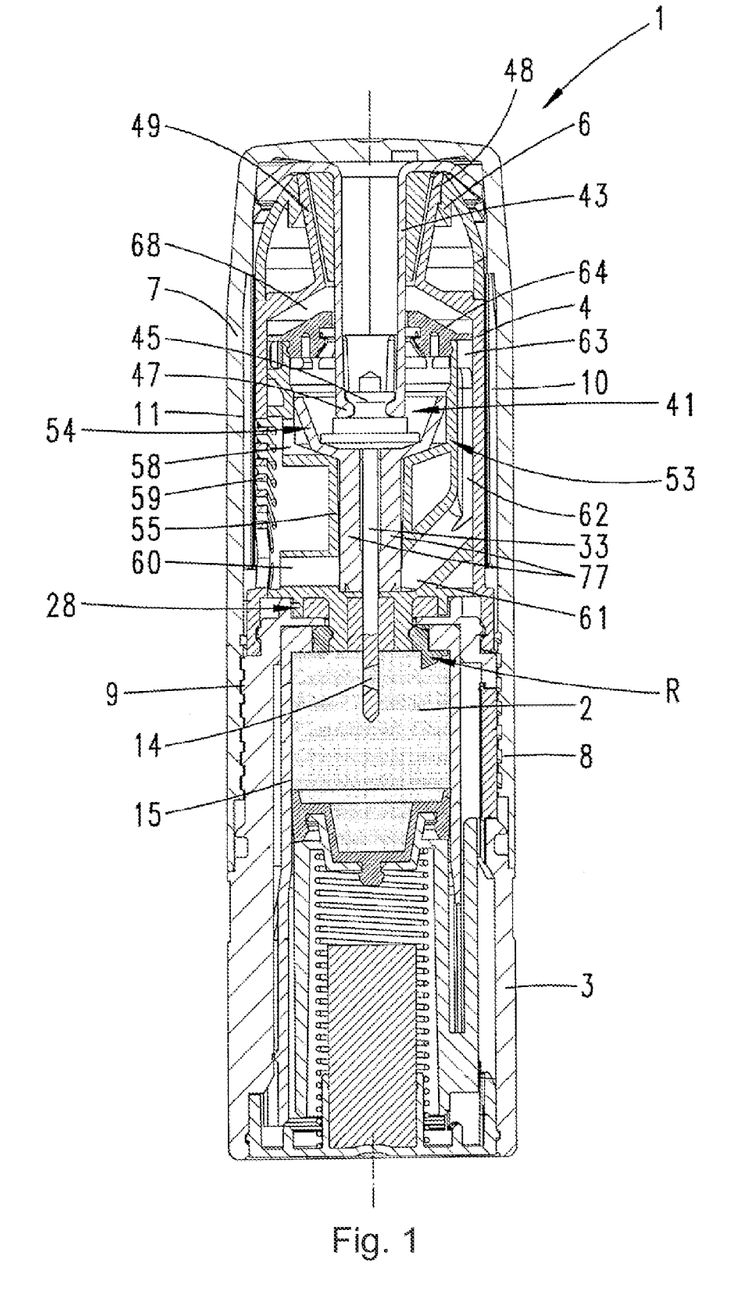
FIG. 1 shows a vertical section through a dosing device which is closed by means of a protective cap.
Figure 2:
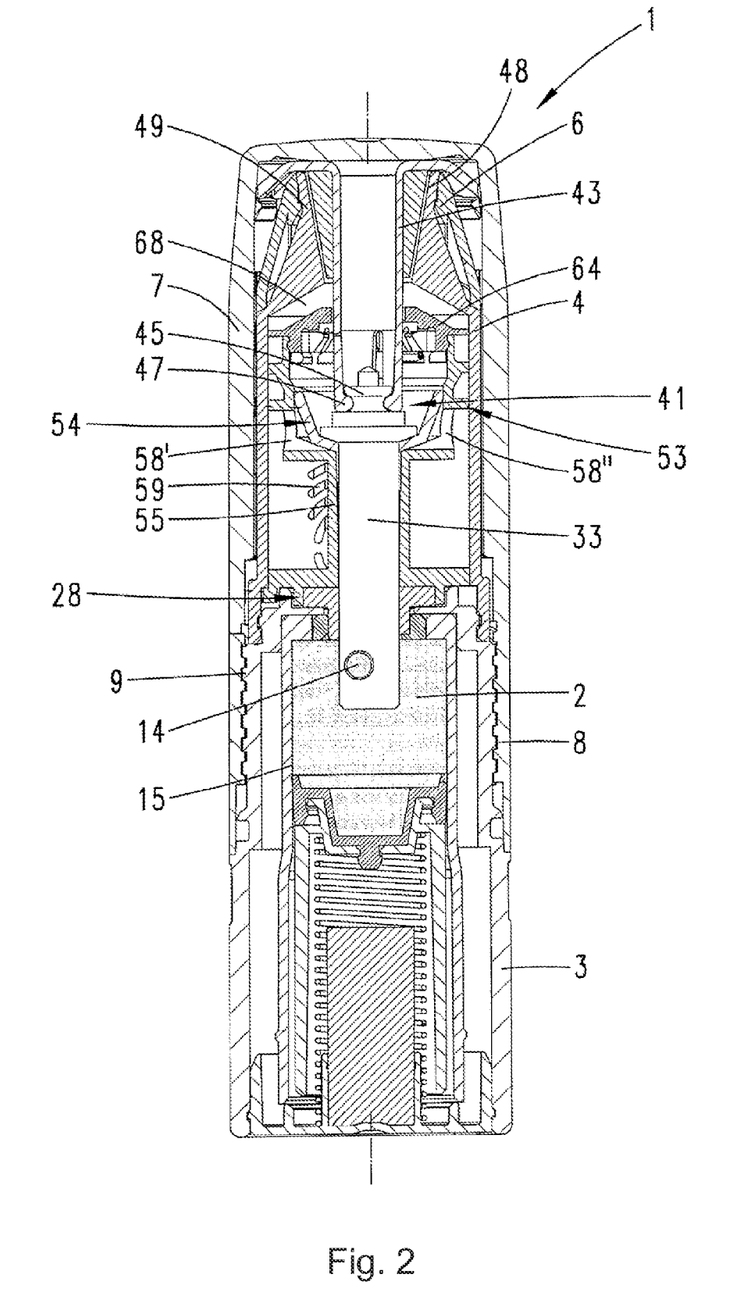
FIG. 2 shows a longitudinal section rotated about 90°, similar to that in FIG. 1.

In the position represented in FIG. 1, just as in the position shown in FIG. 2, the dosing chamber is still situated in the storage chamber 15.

Figure 3:
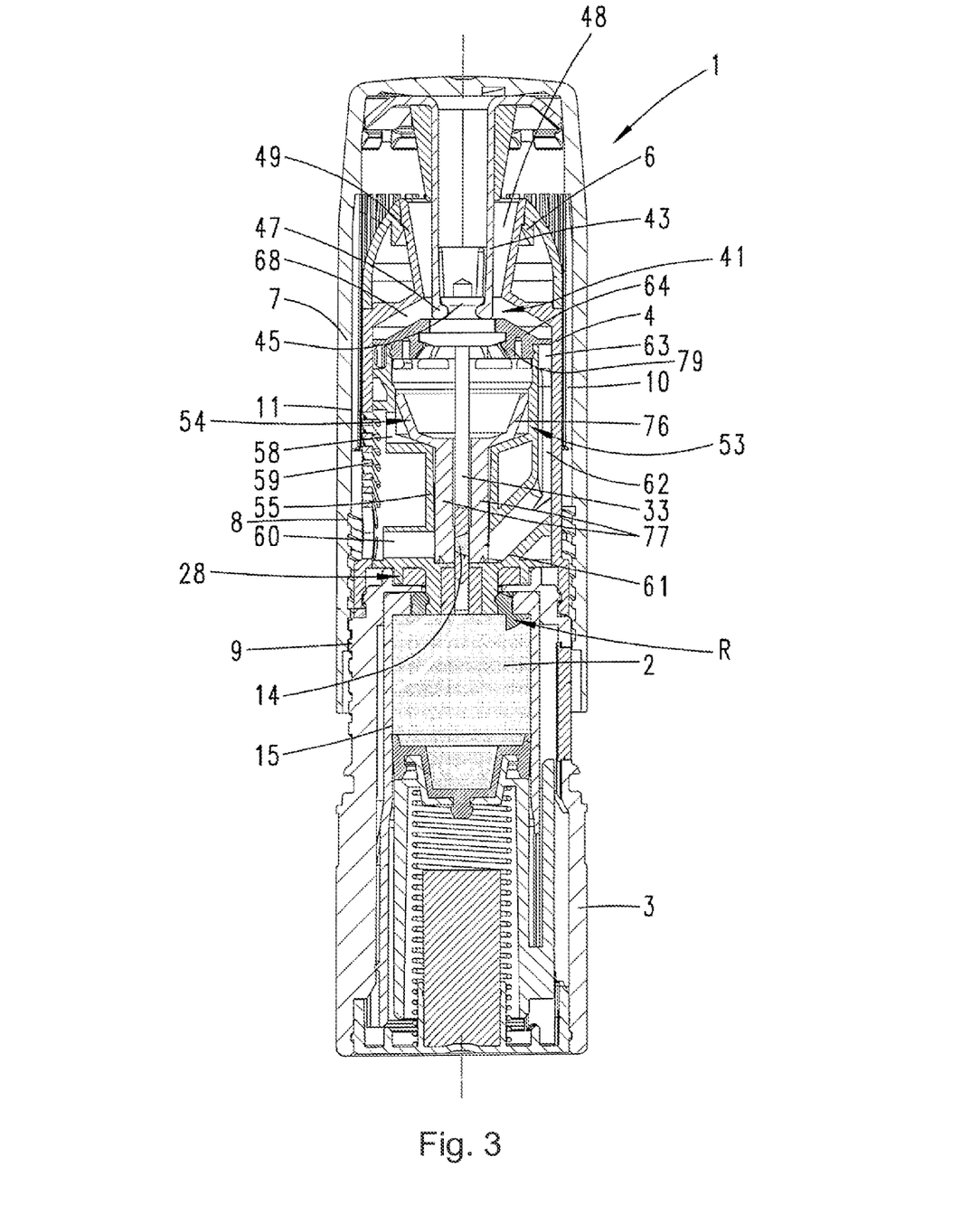
FIG. 3 shows a longitudinal section of the dosing device as the protective cap is being removed.

FIG. 3 shows a partially removed state of the protective cap 7, in which the dosing rod 33 has already been moved completely out of the storage chamber 15.

In this state, however, the dosing chamber 14 is still completely separated from the first gas flow channel 60, 61, 62, 63, 68 by a separating element 54, 76, 77. The separating element has a piston 54 as well as a piston head 76 and tongues 77, which extend on both sides of the dosing rod 33 and cover the dosing chamber 14 on both sides in the position represented.

If the protective cap 7 is twisted off or removed further, the ends of the hollow cylinder 43 expand in a radial manner and the lugs 47 slide out of the annular groove 46 such that the protective cap 7 can be removed further completely. The dosing rod 33 then remains in the drawn-out position and is held there by the latching fingers 79 of the cover part 64.

Figure 4:
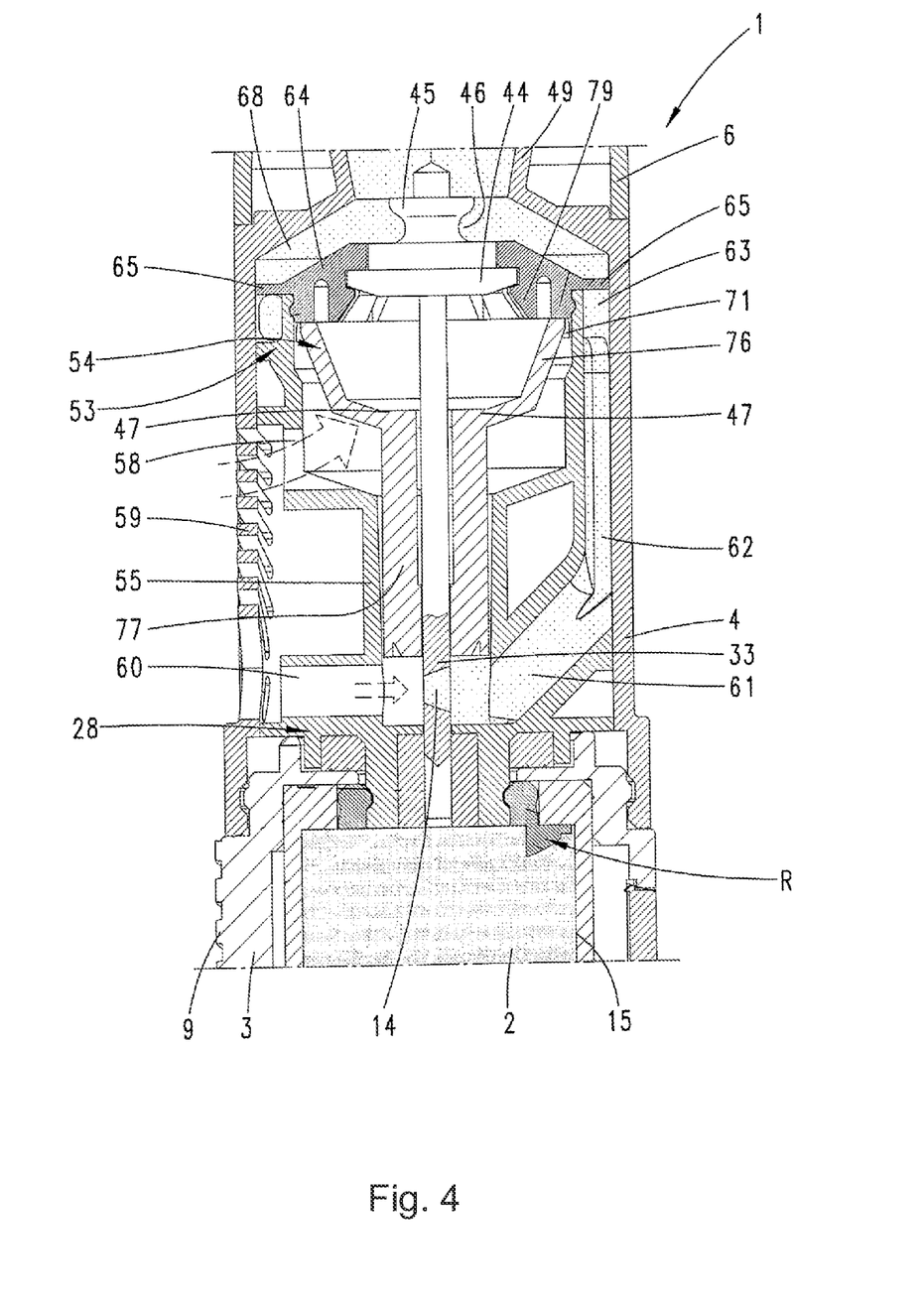
FIG. 4 shows the state of the dosing device once the first gas flow channel has been released by the dosing means release mechanism.
Figure 5:
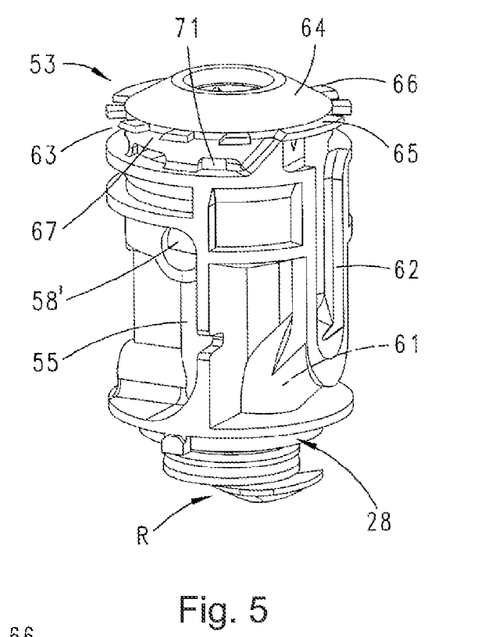
FIG. 5 shows a three-dimensional exterior view of the inside setup of the dosing device.
Figure 6:
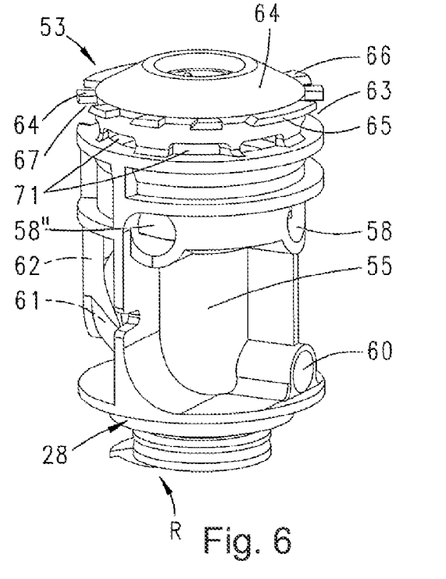
FIG. 6 shows a three-dimensional interior view of the dosing device from a different direction to that in FIG. 5.
Figure 7:
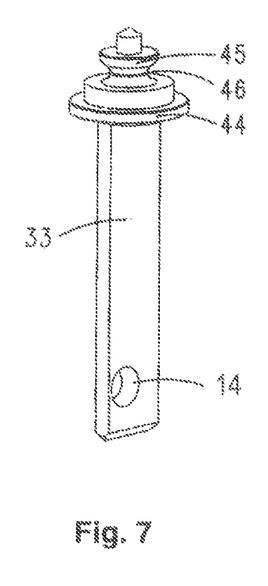
FIG. 7 shows a three-dimensional view of a dosing rod.

If then, once the protective cap has been removed, a suction air stream is generated at the opening of the mouthpiece 6, the results of the same may be explained in more detail by way of FIG. 4. The inner cylinder 53, which is represented, moreover, in a three-dimensional manner in various views from the outside in FIGS. 5 and 6, is designed substantially as a hollow body and guides the tongues 77 of the separating element 54, 76, 77 in the form of a slide guide centrally in a hollow-cylindrical guide portion 55. Following the guide portion 55 is a widened part of the inner cylinder 53, in which the piston head 76, as a tulip-shaped widening of the separating element, is moved. Once the protective cap 7 has been removed, the dosing rod 33 is secured by pulling a radial collar 44 behind latching fingers 79 of the cover part 64.

If air is sucked in via the mouthpiece 6, first of all, through the openings 71 in the inner cylinder 53, the piston 54 is sucked in towards the mouthpiece until it abuts against the underside of the cover part 64. Air can follow from the outside via radial openings 58, 58', 58". The radial openings are connected to a grid wall portion 59 on the outside of the cylinder.

The triggering pressure of the separating element 54, 76, 77, at which said element is pulled in, can be fixed in a reliable manner by means of the development of the slide guide according to the invention, for example to one kilo Pascal. This is effected by means of coating, for example of the separating element, with magnesium stearate powders, which have a specific surface between 2 and 20 square m/gram, in particular between 2.3 and 9.3 square m/gram, preferably between 3 and 8 square m/gram, further preferred between 3 and 5 square m/gram.

The following table shows the test results determined when the invention was being trialed:

| Contact surface between separating element and slide guide element of approximately 46.5 square mm (square millimeters) | Required negative pressure (pressure difference) for actuating the separating element for releasing the dosing chamber |
| --- | --- |
| No coating (untreated) | 3.5 to 4.5 kPa ("kilo Pascal") |
| Specific surface of the MgSt coating of approximately 2.3 square m/gr | 0.5 to 0.8 kPa |
| Specific surface of the MgSt coating of approximately 9.3 square m/gr | 1.8 to 2.1 kPa |

A similar effect can be achieved by providing knobs or webs.

Once the separating element has been pulled in, the annular space of the inner cylinder 53 surrounding the piston head 76 is traversed by a main air flow passing trough the radial openings 58, 58' and 58" and entering the annular chamber 63 through the openings 71.

Through the movement of the piston head 76, the tongues are displaced in the direction towards the mouthpiece 6 and the dosing chamber 14 is consequently released. A gas flow can then flow through the first gas flow channel 60, passing through the dosing chamber 14, into the channel intermediate portion 61 and further axially via the channel 62 into the annular chamber 63, said gas flow entraining the finely distributed active substance 2 out of the dosing chamber 14 and distributing it.

From the annular chamber 63, the gas mixed there with the further air flow from the openings 58, 58', 58" can flow via intermediate spaces 67 on the cover part 64 between and through wings 65, 66 into the annular space 68, turbulence being generated in the peripheral direction of the dosing device, bringing about a further homogeneous fine distribution of the active substance in the gas flow. The gas flow is then relieved in a dispersing part 49 that widens towards the mouthpiece opening 48 and then passes into the mouth cavity of the person sucking in.

Figure 8:
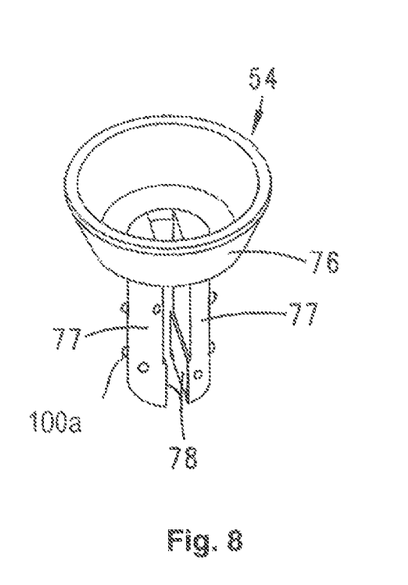
FIG. 8 shows a three-dimensional representation of a separating element.

FIG. 8 provides further detail of the tongues 77 which have sealing faces 78 which are reinforced in their end region and, in the closed position, seal off the dosing chamber 14 in a reliable manner such that, even if the dosing device is shaken, it is not possible for the active substance to drip out of said dosing device.

Knobs 100*a* in the form of circular, rounded elevations are shown in the outer region at the periphery of the tongues 77. The elevations, just as an enhancement with a friction-influencing substance, can also be provided, however, in the region of the piston/of the widening 54 of the separating element, as explained further below. The elevations, just as an alternatively or additionally applied magnesium stearate layer, serve to reduce the friction and/or to make the reproducibility of the friction conditions more precise. Magnesium stearate can also be added to the plastics material separating element as a constituent of the mixture. Typically, powders with a specific surface between 2.3 and 9.3 $m^2/g$ are used and layer thicknesses in the micrometer range are produced in a corresponding manner in the case of a coating.

Figure 9:
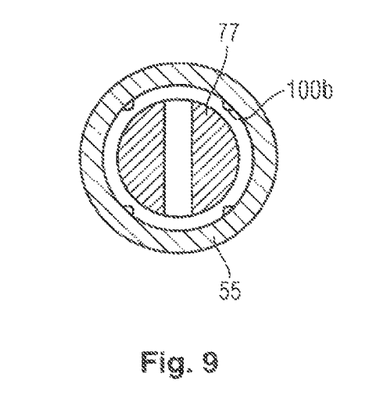
FIG. 9 shows a cross section of a separating element with a slide guide element.

FIG. 9 shows the cross section of a separating element with the tongues 77 which lie in the guide portion 55, in this case the guide portion 55 with a circular cross section having knobs 100*b* for defining the sliding properties in a more precise manner.

Figure 10:
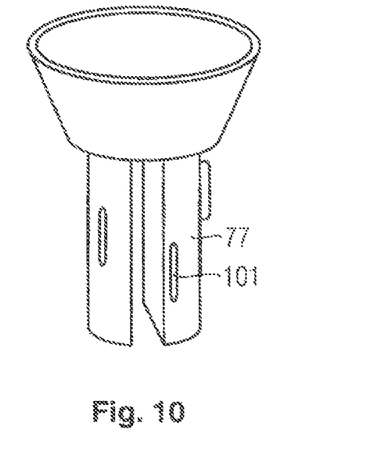
FIG. 10 shows a three-dimensional view of a separating element in an embodiment different from that in FIG. 8.

FIG. 10 finally shows as an embodiment of the invention oblong webs 101, which extend in the direction of movement of the separating element, and which are distributed at the periphery of the tongues 77 and slide on the inner surface of the guide portion 55.

The use, represented above and described in detail, of friction-defining means in the form of a coating of the guide portion 55 or of the tongues 77 or of both parts by means of metal soap, in particular magnesium stearate, or the provision of knobs in the peripheral region of the separating element, in particular at the periphery of the tongues 77, brings about reliable and reproducible defining of the friction properties for the sliding of the separating element in the guide portion and consequently guarantees reliable triggering of the separating element and releasing of the dosing chamber fixed precisely at a moment in time, such that the operating of the dosing device with the generation of a gas flow enriched with an active substance is guaranteed.

Figure 11:
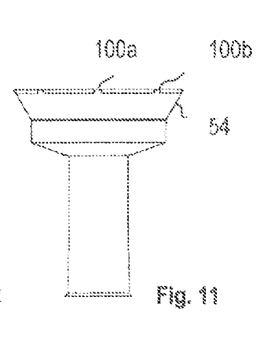
FIG. 11 shows a side view of a separating element with projections on its tulip-shaped widening.
Figures 12, 13:
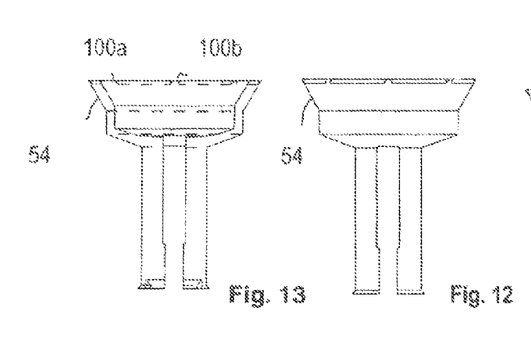
FIG. 12 shows a side view of the separating element of FIG. 11 rotated by 90 degrees.
FIG. 13 shows a sectional side view of the separating element of FIG. 11.
Figure 14:
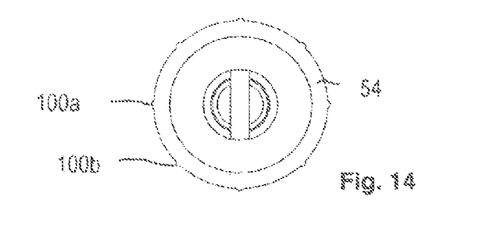
FIG. 14 shows a top view of the separating element from the underside facing the dosing chamber.
Figure 15:
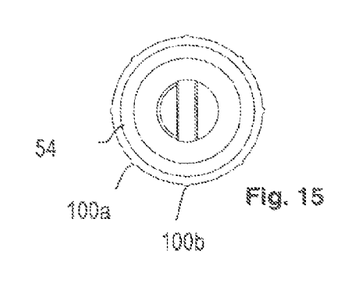
FIG. 15 shows a top view of the separating element of FIG. 11 from the top side facing the mouthpiece and FIG. 16 shows a three-dimensional view of the separating element of FIG. 11.
Figure 16:
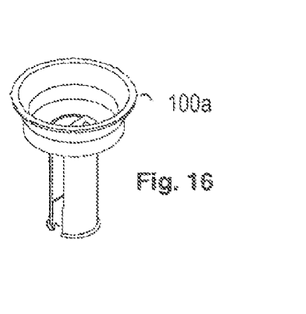

FIG. 11 shows an embodiment of the separating element 54, 76, 77, where the tulip-shaped widening in the form of the piston 54 has radially protruding knobs 100*a*, 100*b*, which are guided in a sliding manner on the inner cylinder 53 in its widened region. In an advantageous manner, 3 to 20 knobs, in particular 6 to 12 knobs can be provided. The knobs can be provided on the upper, outer edge of the widening of the separating element, where said widening abuts directly against the slide guide element in the form of the inner cylinder 53.

The distribution of the knobs and consequently of the slide guide on a short height portion of the separating element effectively prevents the separating element 54, 76, 77 jamming in the slide guide element 53, 55.

A coating with a friction-controlling or friction-reducing substance, such as, for example, magnesium stearate, can be restricted to this region or can extend at least into this region.

The region provided with the knobs or the coating, in this case, is approximately 40 to 50 square mm. In the experiment this proved to be particularly favorable with regard to the required triggering negative pressure, see table above.

FIGS. 12 to 16 show various views of the same embodiment as FIG. 11 from different perspectives, illustrating a preferably symmetrical distribution of the knobs/elevations at the periphery of the separating element and an arrangement in a single row at an identical height.

LIST OF REFERENCES

1 Dosing device
2 Active substance
3 Housing
4 Outer cylinder
6 Mouthpiece
7 Closure flap (protective cap)
8 Internal thread
9 External thread
10 Ribs
11 Grooves
14 Dosing chamber
15 Storage chamber
28 Rotational part
33 Dosing rod
41 Docking point
43 Hollow cylinder
44 Radial collar
45 Latching head
46 Annular groove
47 Lugs
48 Mouthpiece opening
49 Dispersing part
53 Inner cylinder
54 Piston
55 Guide portion
53, 55 Slide guide element
58, 58', 58" Radial openings
59 Grid wall portion
60 Flow channel
61 Channel intermediate portion
62 Channel
63 Annular chamber
64 Cover part
65, 66 Wings
67 Intermediate spaces
68 Annular space
71 Openings
76 Piston head
77 Tongues
79 Latching fingers
100*a*, 100*b* Knobs
101 Webs
R Rotor

The invention claimed is:

1. A dosing device for generating a gas flow with a finely dispersed active substance in said gas flow as a result of a negative pressure applied to a mouthpiece of the dosing device, said dosing device comprising a first gas flow channel and a dosing chamber, which is situated at least sometimes in the region of the first gas flow channel, as well as a dosing chamber release mechanism which has a separating element which can be displaced between a closed position and an open position,
wherein, in the closed position of the separating element, the separating element seals off the dosing chamber, where in the closed position, the first gas flow channel and/or a connection between the first gas flow channel and the dosing chamber is blocked and,
in the open position of the separating element, the separating element no longer seals off the dosing chamber, where in the open position, the first gas flow channel and/or the connection between the first gas flow channel and the dosing chamber is released, and
further comprising a slide guide element
on which the separating element is displaceable along a sliding contact region between the closed position and the open position, the separating element remaining in sliding contact with the slide guide element as the sliding element is displaced and
on which the separating element is driveable by means of the negative pressure applied at the mouthpiece, and
wherein the separating element or the slide guide element is provided at least in the sliding contact region with a slide element that influences the sliding friction properties.

2. The dosing device as claimed in claim 1, characterized in that the separating element is cup-shaped and in that the slide element is provided in that part of the separating element that is widened in a cup-shaped manner.

3. The dosing device as claimed in claim 1, characterized in that the slide element is formed by an enhancement of the separating element and/or of the slide guide element in the surface region with a friction-reducing substance.

4. The dosing device as claimed in claim 3, characterized in that the separating element and/or the slide guide element contain the friction-reducing substance as an ingredient of a mixture.

5. The dosing device as claimed in claim 3, characterized in that the separating element and/or the slide guide element are coated with the friction-reducing substance.

6. The dosing device as claimed in claim 3, characterized in that the friction-reducing substance is a powder.

7. The dosing device as claimed in claim 3, characterized in that the friction-reducing substance comprises a metal soap.

8. The dosing device as claimed in claim 7, characterized in that the metal soap comprises a specific surface area between 2 and 20 square m/g, in particular between 3 and 8 square m/g, further preferred between 3 and 5 square m/g. is formed by a surface contour that has projections.

9. The dosing device as claimed in claim 1, characterized in that the slide element is formed by a surface contour comprising a plurality of projections.

10. The dosing device as claimed in claim 9, characterized in that the surface contour comprises at least one knobs.

11. The dosing device as claimed in claim 10, characterized in that the surface contour comprises between 5 and 13 knobs.

12. The dosing device as claimed in claim 9, characterized in that the surface contour comprises webs which extend substantially in the sliding direction.

13. The dosing device as claimed in claim 9, characterized in that the projections are rounded in the region of contact with a sliding partner.

14. The dosing device as claimed in claim 9, characterized in that a height of the plurality of projections is the same.

15. The dosing device as claimed in claim 1, characterized in that
the slide element is formed by a surface contour having a plurality of projections and an enhancement of the separating element and/or of the slide guide element in the surface region with a friction-reducing substance.

* * * * *